United States Patent
Weathers, Jr. et al.

(10) Patent No.: US 6,837,710 B2
(45) Date of Patent: Jan. 4, 2005

(54) BENT TIP DENTAL ROOT CANAL IMPLEMENT AND METHOD THEREOF

(76) Inventors: Arthur Kitchings Weathers, Jr., 14 Hudson Rd., Griffin, GA (US) 30224; Michael Douglas Goldstein, 474 N. Rover Rd., Williamson, GA (US) 30292

( * ) Notice: Subject to any disclaimer, the term of this patent is extended or adjusted under 35 U.S.C. 154(b) by 51 days.

(21) Appl. No.: 10/206,463

(22) Filed: Sep. 30, 2002

(65) Prior Publication Data

US 2004/0063066 A1 Apr. 1, 2004

(51) Int. Cl.⁷ .............................................. A61C 3/00
(52) U.S. Cl. ....................... 433/157; 433/102; 140/105
(58) Field of Search ................................ 433/141, 102, 433/4, 157, 159, 224; 140/105, 106

(56) References Cited

U.S. PATENT DOCUMENTS

| | | | | |
|---|---|---|---|---|
| 548,263 A | * | 10/1895 | Morgan | 140/105 |
| 896,170 A | * | 8/1908 | Stout | 140/105 |
| 3,357,460 A | * | 12/1967 | Gawura | 140/106 |
| 3,993,108 A | * | 11/1976 | Kirschenman et al. | 140/105 |
| 4,109,383 A | * | 8/1978 | Reed et al. | 433/72 |
| 4,708,651 A | * | 11/1987 | Buchanan | 433/157 |
| 4,716,757 A | * | 1/1988 | McGregor et al. | 72/387 |
| 5,110,291 A | * | 5/1992 | Randin | 433/156 |
| 5,197,880 A | * | 3/1993 | Lovaas | 433/159 |
| 5,295,827 A | * | 3/1994 | Fundingsland et al. | 433/80 |
| 5,395,236 A | * | 3/1995 | Khouri | 433/4 |

FOREIGN PATENT DOCUMENTS

CH        680043 A5  *  6/1992

* cited by examiner

Primary Examiner—Ralph A. Lewis

(57) ABSTRACT

This application relates to the field of Dentistry, and in more particular to the use of root canal excavating implements such as files, broaches, reamers, or probes employed for the use of clearing tissue and removing dentin from the nerve canal of teeth. An introduced bent tip of 45 degrees to the angle of the implement, at a distance as close as a half of one millimeter from the leading tip, is cited as an improved means to get the tip of the implement to the desired working length.

16 Claims, 1 Drawing Sheet

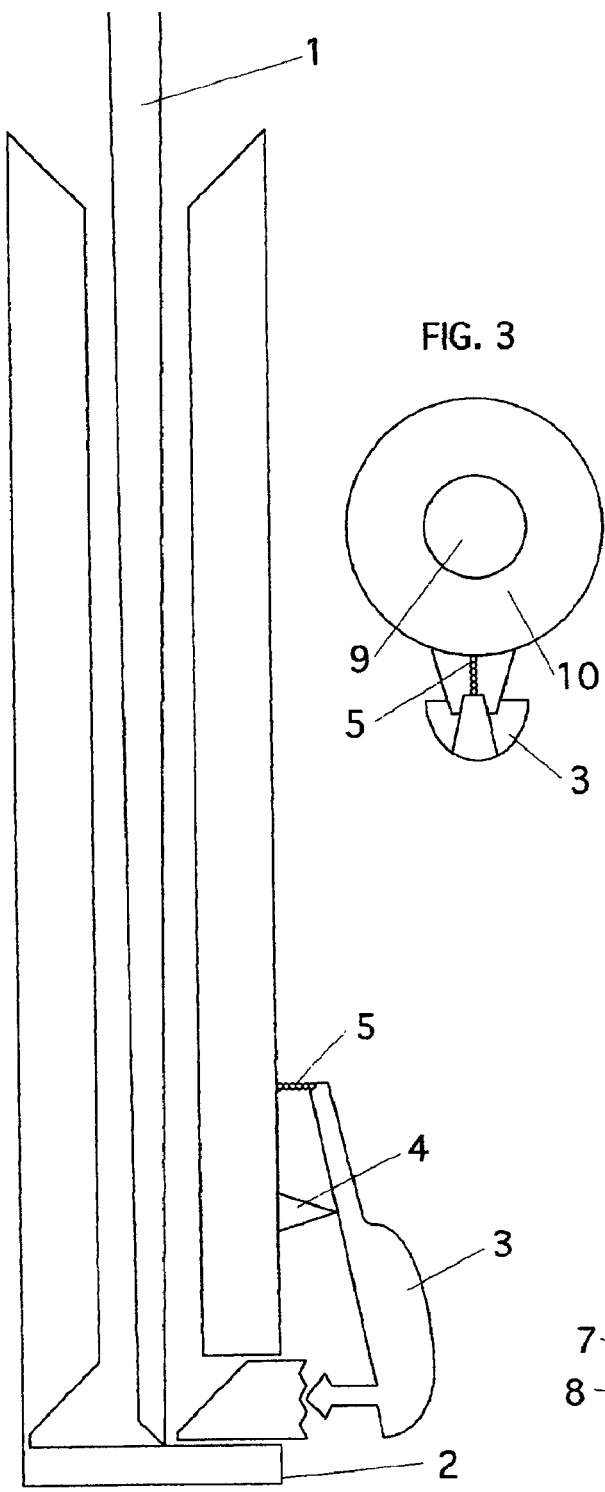
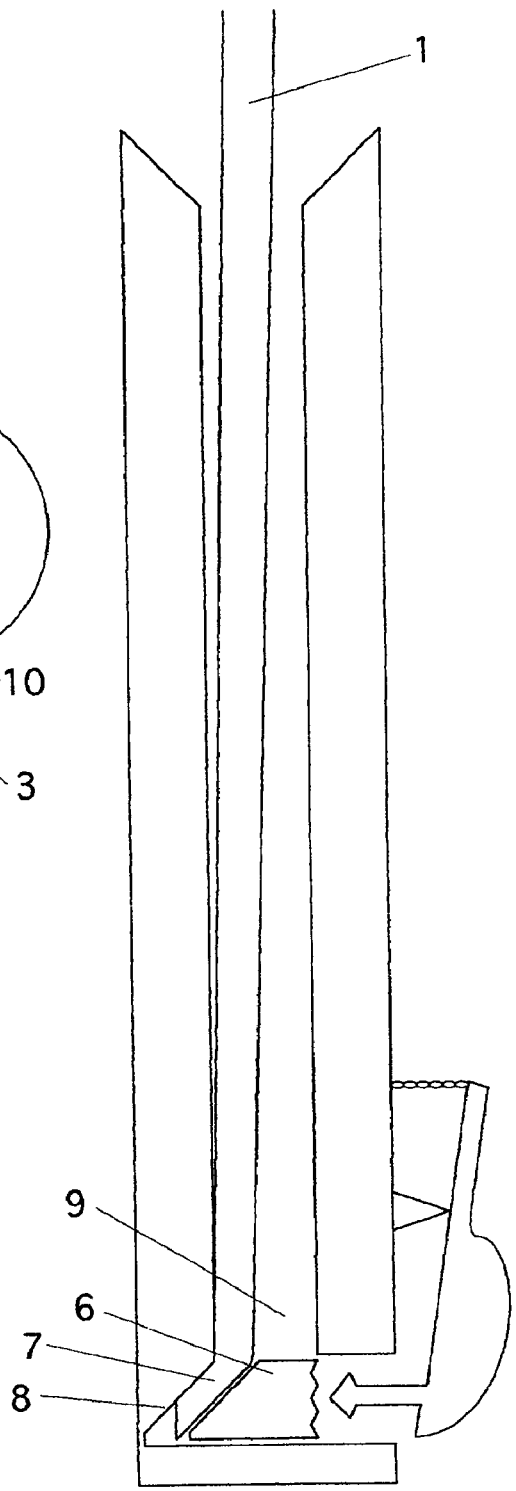

BENT TIP DENTAL ROOT CANAL IMPLEMENT AND METHOD THEREOF

FIELD OF THE INVENTION

This application relates to the field of Dentistry, and in more particular to the use and limitations of root canal excavating implements such as files, broaches, reamers, or probes dedicated to the particular use of clearing tissue from the nerve canal of teeth.

DESCRIPTION OF THE RELATED ART

Due to the small diameter of dental root canal implements, manufacturers have uniformly provided materials of strength designed primarily to prevent capture by the tooth, and subsequent breakage. The easiest shape to accommodate retrieval of the implement is a straight design. However, due to the varying sizes and shapes of the canal itself of various individuals, the straight tip of the implement is often impeded from complete penetration of the entire length of the tooth. When encountering this situation Dentists have no recourse but to temporarily stop the root canal procedure and withdraw the implement. Subsequently, another implement (either thinner or of another variety) may then be reintroduced into the canal to see if the alternate implement will now pass to the required depth to continue in tissue removal.

BRIEF SUMMARY OF THE INVENTION

The use of a bevy of straight root canal implements of diminishing circumference has long been the method of choice for dentists for root canal procedure. Herein is cited a controlled crimping apparatus allowing the introduction of a precise 45 degree angle as close as a half a millimeter from the contact tip of an implement. With a micro size, this improvement can be difficult to see with the naked eye. On contact with hard surfaces such as the inner dentin of the canal, the bent tip implement will usually flex and bend away from the obstruction and will continue deeper into the canal with further pressure from a dentist.

It is therefore accordingly an object of the present invention to provide a pre-fabricated dental root canal implement bearing a 45 degree bent tip, or to provide the means for a dentist to insert a straight implement into an object of manufacture that will accomplish the bending under the prescribed conditions.

It is therefore further accordingly an object of the present invention to provide an optimized deflection for a dental implement when an inner dentin surface is reached, thus also serving as a time saving means to reduce the times a dentist encounters the need to interrupt an ongoing procedure when reaching an obstruction with a particular implement.

BRIEF DESCRIPTION OF THE DRAWINGS

FIG. 1 is a bending sheath 2 with finger operated pivot to introduce a calculated angle in the tip of a dental root canal instrument 1.

FIG. 2 is the same bending sheath after finger pressure has been applied.

FIG. 3 is an entry end view of the bending sheath without instrument 1.

DETAILED DESCRIPTION OF THE INVENTION

In FIG. 1 a dental root canal implement 1 is inserted into and comes to rest against the end of a bending sheath 2. A finger pad 3 allows pressure to be applied over hinge 4 against the resistance of soft spring 5. As seen in FIG. 2 after finger pressure is applied, the motile wedge 6 torques the tip 7 of implement 1 against the inner impression wall 8 of sheath 2 sufficient to form a 45 degree angle. The inner width of the sheath canal 9 is of a large enough measure to allow the bent tip to be withdrawn as the implement is removed. The entry end 10 of the sheath is funnel shaped to guide the instrument successfully to the entrance opening of canal 9.

Although the invention is shown as a best embodiment for in situ use within a dentist's office, the concept can be adapted to a manufacturing environment where the described bent tip may be formed as a step in the overall manufacturing process of the implement. Any process or means to bend the tip is contemplated, but a crimping motile wedge moving against an impression surface is cited as the best embodiment.

The cited 45 degree bending to be applied to the implement is also a best embodiment value. Greater or lesser angles of degree will work for the intended purpose with varying chances for success. The selected spot to apply the bend is also recommended as about one millimeter from the tip itself, but this also can be varied by design.

This invention should not be confined to the embodiments described, as many modifications are possible to one skilled in the art. This paper is intended to cover any variations, uses, or adaptations of the invention following the general principles as described and including such departures that come within common practice for this art and fall within the bounds of the claims appended herein.

We claim:

1. A crimping apparatus for the generation of an angled bend in a shaft of a dental implement that is used for clearing tissue from the root canals of teeth, comprising:

an elongated tubular containment member having an open end for receiving the shaft of said dental implement and an opposite closed end for contacting the tip of said dental implement's shaft when fully inserted into the containment member, an impression surface formed at the closed end of the containment member, and a wedge at the closed end of the tubular containment member moveable toward the impression surface for bending the tip of an inserted dental implement to a particular angle and at a particular point on the shaft near the tip of the dental implement.

2. The apparatus of claim 1, where said particular angle is 45 degrees, within a tolerance of 35 degrees of error.

3. The apparatus of claim 1, where said particular angle is 45 degrees, within a tolerance of 25 degrees of error.

4. The apparatus of claim 1, where said particular angle is 45 degrees, within a tolerance of 20 degrees of error.

5. The apparatus of claim 1, where said particular angle is 45 degrees, within a tolerance of 15 degrees of error.

6. The apparatus of claim 1, where said particular angle is 45 degrees, within a tolerance of 10 degrees of error.

7. The apparatus of claim 1, where said particular angle is 45 degrees, within a tolerance of 5 degrees of error.

8. The apparatus of claim 1,
where said particular point is a distance of approximately one millimeter from the extreme end of said leading tip, with an error tolerance of 0.6 millimeters.

9. The apparatus of claim 1,
where said particular point is a distance falling anywhere from approximately 1.5 millimeters from the extreme end of said leading tip to approximately 2.3 millimeters from the extreme end of said leading tip.

10. The apparatus of claim 1,
where said dental implement is one of the categories of files, broaches, reamers, or probes.

11. A method for bending the tip of a dental implement used for clearing tissue from the root canals of teeth,
with the step where said tip of said implement is inserted into a crimping apparatus having the capacity to bend said tip under command,
where the step of generating said command is completed,
where the step of removing said implement from said apparatus is completed,
where the bending of said tip is the introduction of a 45 degree bend along said tip about one half of a millimeter from the actual end of said implement, where said 45 degree bend is within a tolerance of 25 degrees of error.

12. The method of claim 11,
where said angle of 45 degrees is within a tolerance of 20 degrees of error.

13. The method of claim 11,
where said angle of 45 degrees is within a tolerance of 15 degrees of error.

14. The method of claim 11,
where said angle of 45 degrees is within a tolerance of 10 degrees of error.

15. The method of claim 11,
where said angle of 45 degrees is within a tolerance of 5 degrees of error.

16. The method of claim 11, said crimping apparatus having containment means to position said implement,
said crimping apparatus having a motile wedge activated by pressure,
said crimping apparatus having an impression surface,
whereby said motile wedge is activated by an operator to approach against said impression surface sufficiently close to bend said implement.

* * * * *